(12) United States Patent
Wellendorf et al.

(10) Patent No.: US 10,350,104 B2
(45) Date of Patent: Jul. 16, 2019

(54) ORTHOPEDIC BRACE AND METHOD OF MAKING THE SAME

(71) Applicant: Scott Specialties, Inc., Belleville, KS (US)

(72) Inventors: Timothy E. Wellendorf, Ft. Lauderdale, FL (US); Melva Nondorf, Belleville, KS (US); Melissa Novak, Narka, KS (US); Teresa Champlin, Concordia, KS (US)

(73) Assignee: Scott Specialties, Inc., Belleville, KS (US)

( * ) Notice: Subject to any disclaimer, the term of this patent is extended or adjusted under 35 U.S.C. 154(b) by 548 days.

(21) Appl. No.: 14/800,348

(22) Filed: Jul. 15, 2015

(65) Prior Publication Data

US 2017/0014257 A1   Jan. 19, 2017

(51) Int. Cl.
*A61F 5/01* (2006.01)
*A61F 5/058* (2006.01)

(52) U.S. Cl.
CPC ........ *A61F 5/05866* (2013.01); *A61F 5/0102* (2013.01); *A61F 5/0104* (2013.01); *A61F 5/013* (2013.01); *A61F 5/0118* (2013.01)

(58) Field of Classification Search
CPC .......... A61F 5/0118; A61F 5/013; A61F 5/10; A61F 5/058; A61F 5/05825; A61F 5/05858; A61F 5/05866; A61F 13/10; A61F 13/104; A61F 13/107; A61F 13/108; A61F 5/01; A61F 5/0102; A61F 5/0104; A61F 5/0109; A61F 5/05875; A61F 5/05841; A61F 5/37; A61F 5/3723; A61F 5/373; A61F 5/3738; A61F 5/3746; A61F 13/08; A61F 13/085; A61F 13/0102; A61F 13/0105
See application file for complete search history.

(56) References Cited

U.S. PATENT DOCUMENTS

| 949,716 | A | | 2/1910 | Quenzer |
| 3,512,776 | A | | 5/1970 | Thomas |
| 4,040,632 | A | | 8/1977 | Pawl |
| 4,183,098 | A | | 1/1980 | Knowles, Jr. |
| 4,441,490 | A | | 4/1984 | Nirschl |
| RE32,566 | E | | 12/1987 | Patton, Jr. |
| 4,716,892 | A | * | 1/1988 | Brunswick ............ A61F 5/0118 602/21 |

(Continued)

*Primary Examiner* — Alireza Nia
*Assistant Examiner* — Rachel A Berezik
(74) *Attorney, Agent, or Firm* — Erickson Kernell IP, LLC; Aaron S. Reed

(57) ABSTRACT

An orthopedic brace and method of making the same includes a wrap member having a first and second layer. The first layer includes a first sheet and a second sheet in a laterally spaced apart relationship. Each sheet has an inner side edge and an inner panel portion which extends the length of the corresponding sheet along the corresponding inner side edge. The second layer has first and second side edges, a first overlay portion extending the length of the second layer adjacent the first side edge and overlapping the first sheet's panel portion, a second overlay portion extending the length of the second layer adjacent the second side edge and overlapping the second sheet's panel portion, and a center portion that bridges the overlay portions. The layers are stitched together along spaced apart sets of seams.

11 Claims, 7 Drawing Sheets

(56) References Cited

U.S. PATENT DOCUMENTS

| | | | |
|---|---|---|---|
| 4,854,309 A * | 8/1989 | Elsey | A61F 5/0118 602/21 |
| 5,072,725 A | 12/1991 | Miller | |
| 5,160,314 A | 11/1992 | Peters | |
| 5,388,273 A | 2/1995 | Sydor et al. | |
| 5,426,791 A | 6/1995 | Sydor et al. | |
| 5,484,392 A | 1/1996 | Sydor et al. | |
| 6,142,966 A | 11/2000 | Hely | |
| 6,190,344 B1 | 2/2001 | Bobroff | |
| 6,196,985 B1 | 3/2001 | Slautterback | |
| 6,383,157 B1 | 5/2002 | Massi et al. | |
| D461,600 S | 8/2002 | Domanski et al. | |
| 6,561,994 B1 * | 5/2003 | Mills | A61F 5/0118 602/20 |
| 7,033,331 B1 * | 4/2006 | Hely | A61F 5/0118 128/878 |
| 7,037,286 B1 | 5/2006 | Reinhardt | |
| 7,276,039 B2 * | 10/2007 | Garelick | A61F 5/0118 602/21 |
| 7,402,149 B1 * | 7/2008 | Garelick | A61F 5/0118 128/879 |
| 7,568,238 B2 | 8/2009 | Schossberger et al. | |
| 7,780,614 B2 | 8/2010 | Bruce et al. | |
| 8,398,573 B2 | 3/2013 | Howard | |
| 2003/0191421 A1 | 10/2003 | Weaver, II et al. | |
| 2008/0119771 A1 * | 5/2008 | Jaccard | A61F 5/0118 602/5 |
| 2008/0287848 A1 * | 11/2008 | Jaccard | A61F 5/0118 602/21 |
| 2013/0211304 A1 * | 8/2013 | Romo | A61F 5/013 602/21 |

* cited by examiner

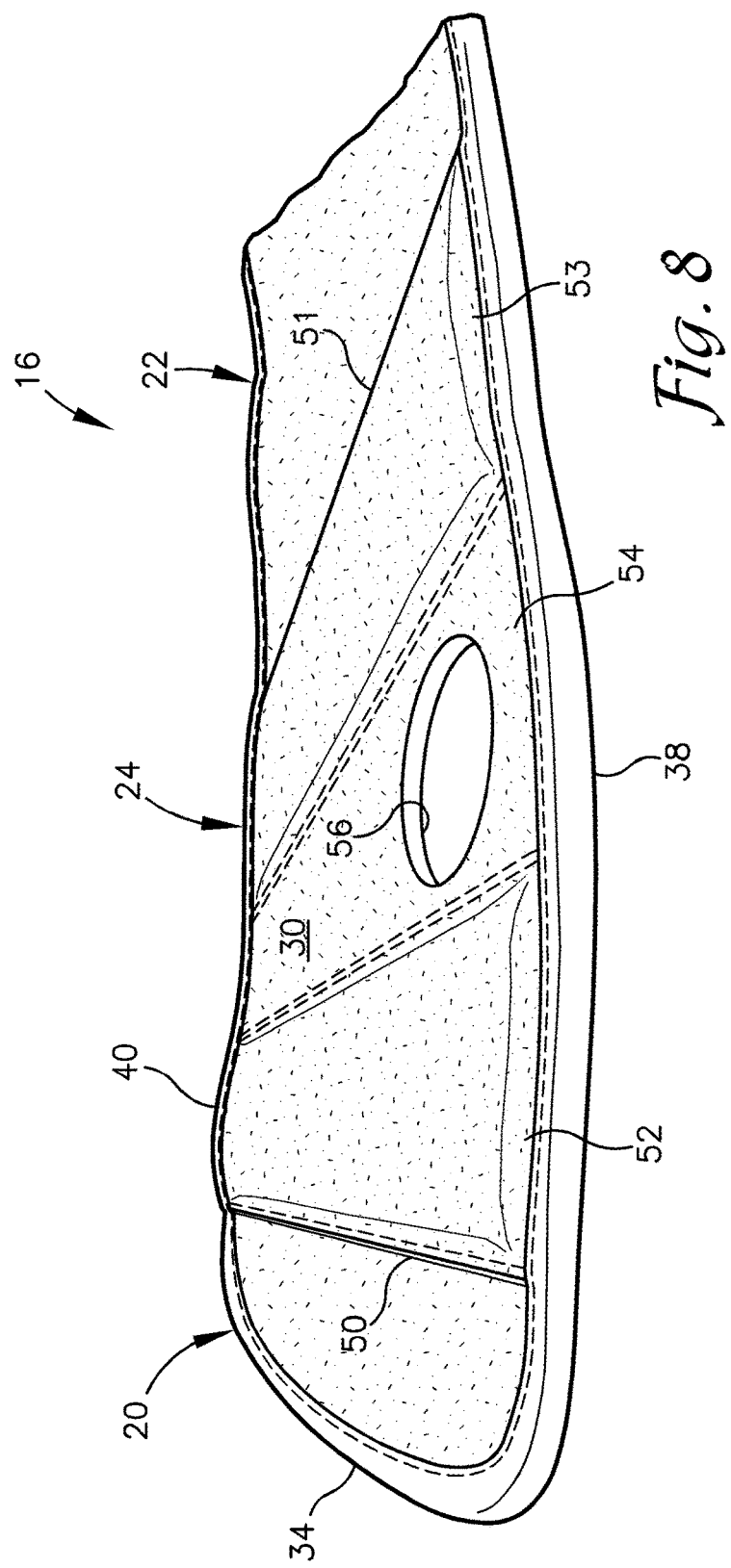

ORTHOPEDIC BRACE AND METHOD OF MAKING THE SAME

BACKGROUND OF THE INVENTION

This invention relates generally to wrist braces and more particularly to an improved, simple, stretchable wrist brace that can be used on either wrist of the wearer and allows easy manipulation of the brace by the user with the other hand. While many braces can only be used on a specified right wrist or left wrist, this brace is adaptable to be used with either wrist. It is an ambidextrous brace. This invention further relates to a method of making an orthopedic brace. More specifically, it relates to a method of forming a stay pocket for various types of orthoses. A continuous need exists for simple, effective wrist orthoses as well as methods of making various orthoses which incorporate the advantages that are embodied in this brace the method of making it.

SUMMARY OF THE INVENTION

Embodiments of the invention are defined by the claims below, not this summary. A high-level overview of various aspects of the invention are provided here for that reason, to provide an overview of the disclosure, and to introduce a selection of concepts that are further described in the Detailed Description section below. This summary is not intended to identify key features of essential features of the claimed subject matter, nor is it intended to be used as an aid in isolation to determine the scope of the claimed subject matter.

In view of the foregoing, a primary object of the present invention is to provide a wrist brace that can be worn on either the right or left wrist of a user.

Another primary object of the present invention is to provide a wrist brace that is easy for the user to put on and take off.

Still another primary object of the present invention is to provide a method of making orthopedic braces that minimizes sewing time.

Still another primary object of the present invention is to provide a method of making orthopedic braces that require fewer components and thus provide a cost savings in medical grade material.

Yet another object of the present invention is to provide a method of making orthopedic braces with a clean appearance.

Yet another object of the present invention is to provide a wrist brace that is comfortable for the user.

These and other objects and advantages of the invention are obtained by providing an orthopedic brace having a wrapping member with a first layer and a second layer. The first layer includes a first sheet and a second sheet in a laterally spaced apart relationship, each sheet having an inner side edge, an inner panel portion, and an outer side edge. Each inner panel portion extends the length of the corresponding sheet adjacent the corresponding inner side edge. The outer side edges form opposite ends of the base member. The second layer has first and second side edges, with a first overlay portion that extends the length of the second layer adjacent the first side edge and overlaps the panel portion of the first sheet, and a second overlay portion that extends the length of the second layer adjacent the second side edge and overlaps the panel portion of the second sheet, and with a center portion that extends between the overlay portions. The brace also includes a member for securing the first layer to the second layer.

These objects and advantages are also obtained by providing a method of making an orthopedic brace by positioning a first base sheet and a second base sheet in a laterally spaced apart relationship, with the inner side edges of each base sheet being substantially parallel, positioning a side portion of an overlay sheet over an inner portion of the first base sheet and the overlay sheet's opposite side portion over an inner portion of the second base sheet, securing the first base sheet and the overlay sheet together along a pair of parallel seams, one seam extending along the overlay sheet's first side edge and the other seam extending along the first base sheet's inner side edge, to form a first stay pocket and securing the second base sheet and the overlay sheet together along a second pair of parallel seams, one seam extending along the overlay sheet's second side edge and the other seam extending along the second base sheet's inner side edge, to form a second stay pocket.

DESCRIPTION OF THE DRAWINGS

Illustrative embodiments of the invention are described in detail below with reference to the attached drawing figures, and wherein:

FIG. 8 is a partial perspective of the outer surface of the brace.

DETAILED DESCRIPTION

The subject matter of the invention is described with specificity herein to meet statutory requirements. But the description itself is not intended to necessarily limit the scope of the claims. Rather, the claimed subject matter might be embodied in other ways to include different components, steps, or combinations thereof similar to the ones described in this document, in conjunction with other present or future technologies. Terms should not be interpreted as implying any particular order among or between various steps herein disclosed unless and except when the order of individual steps is explicitly described.

Figure 1:
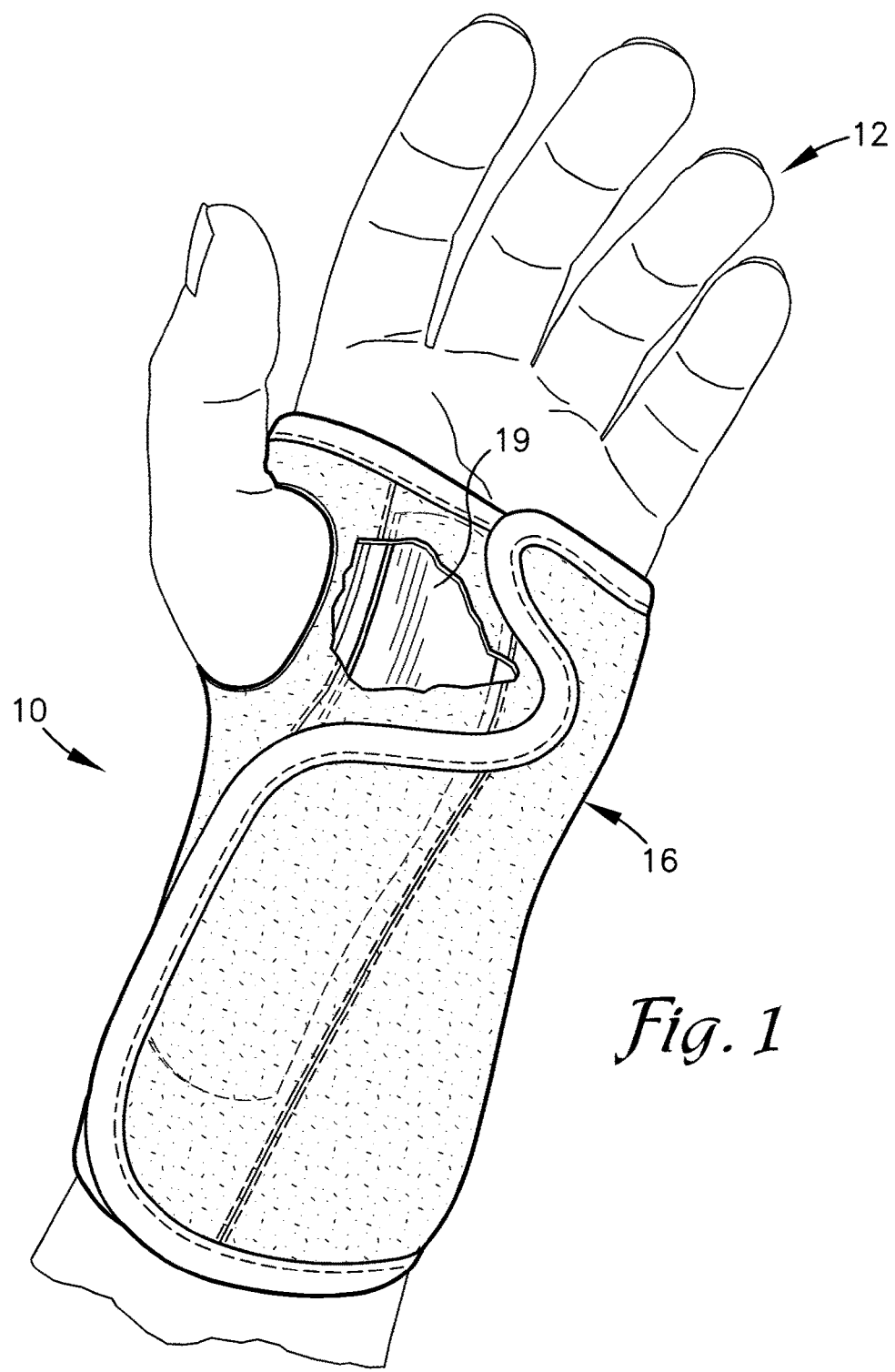
FIG. 1 is a perspective view of the brace as worn on the left hand of a user, partially broken away to show the stay support therein.
Figure 2:
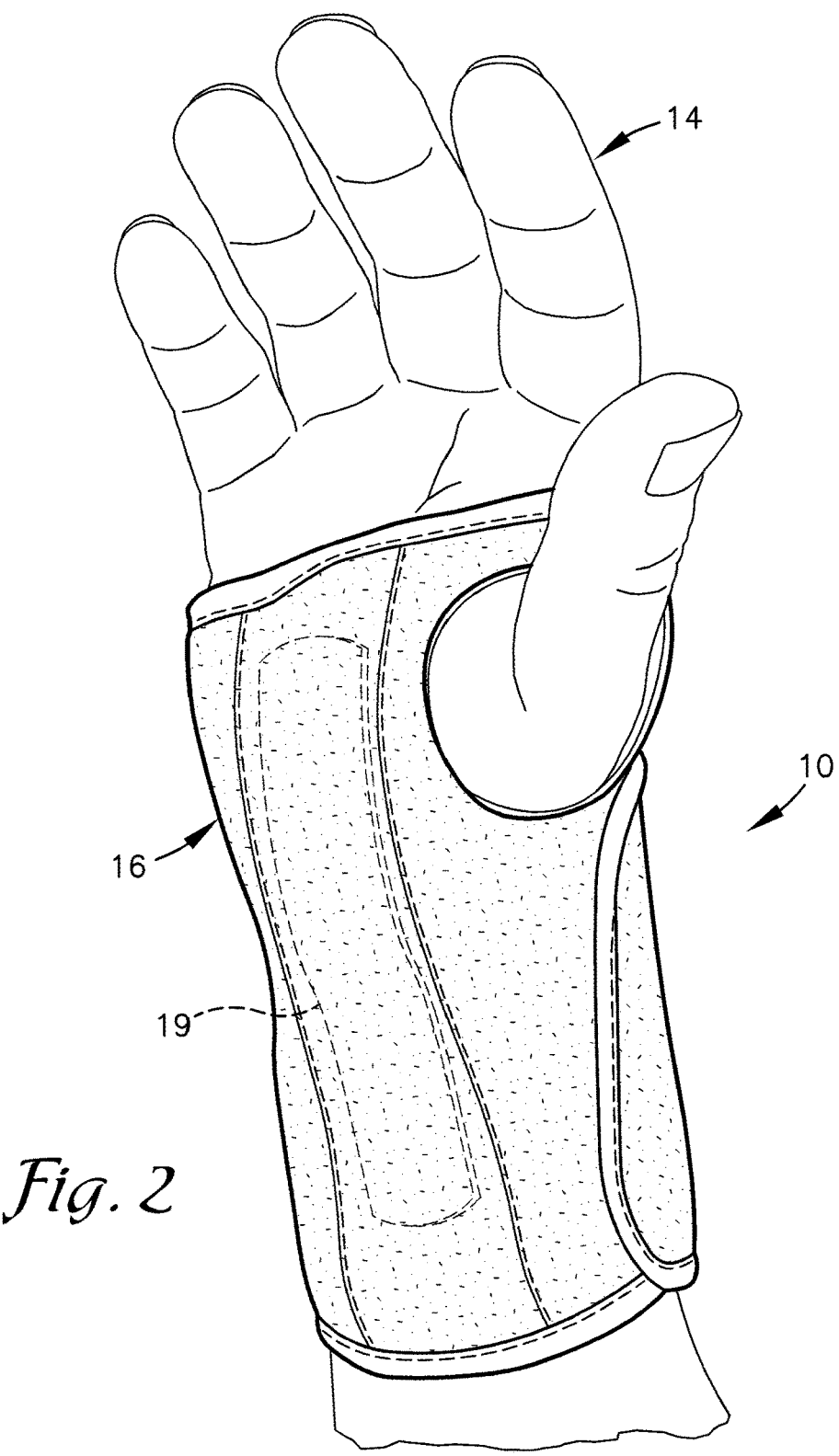
FIG. 2 is a perspective view of the brace as worn on the right hand of a user, with the stay shown in phantom lines.
Figure 3:
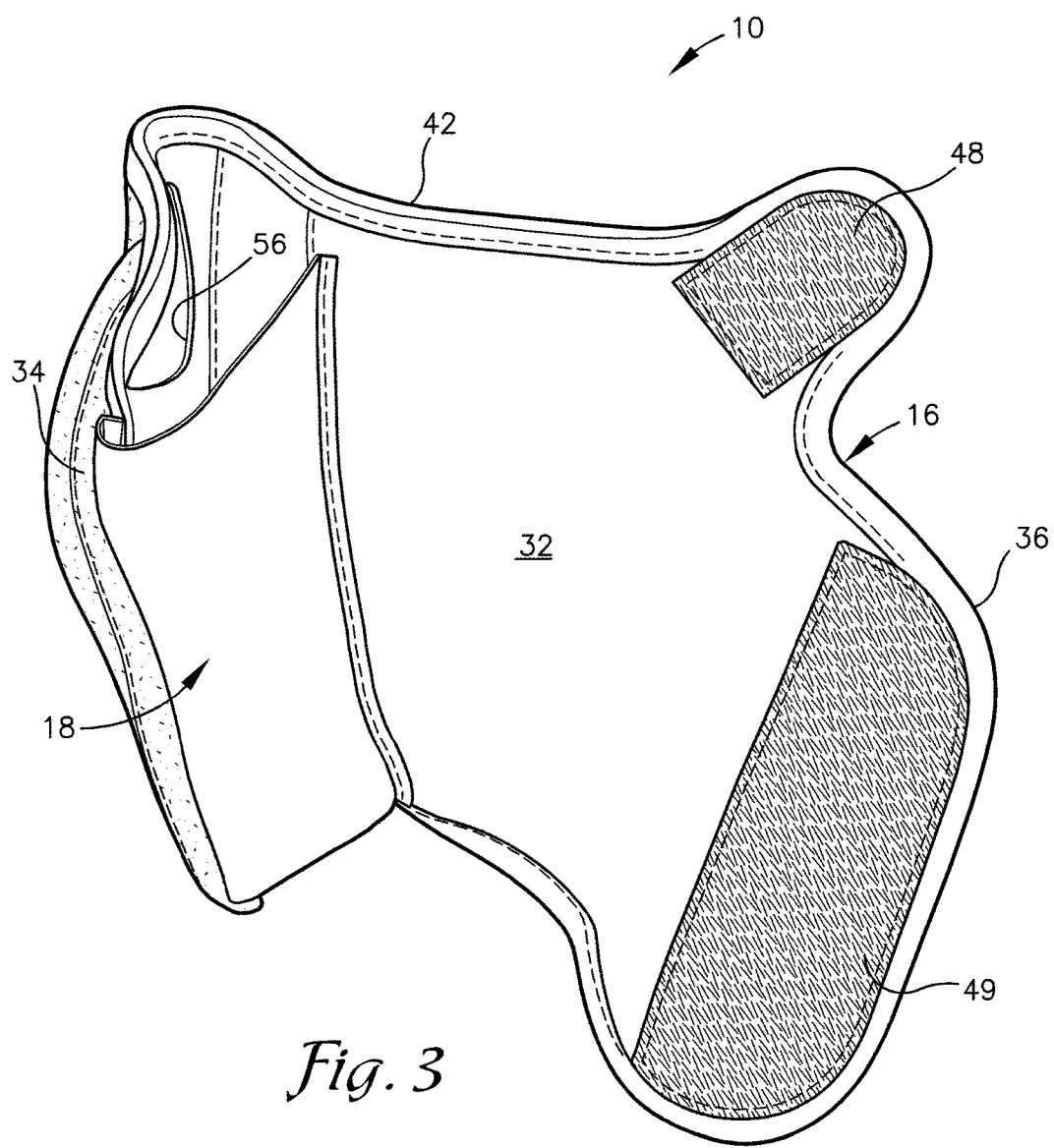
FIG. 3 is a perspective view of the inner side of the brace.

With reference to FIGS. 1-3, an orthopedic brace 10 is depicted. The brace 10 can be worn on either the left hand 12, as in FIG. 1, or the right hand 14, as in FIG. 2, of a user, to aid in recovery from wrist or hand injuries. The brace 10 includes a wrap member 16, wrist webbing 18 and a stay 19. Depending on which wrist or hand is injured, the stay 19 is selectively positioned to support the injured wrist.

Figure 5:
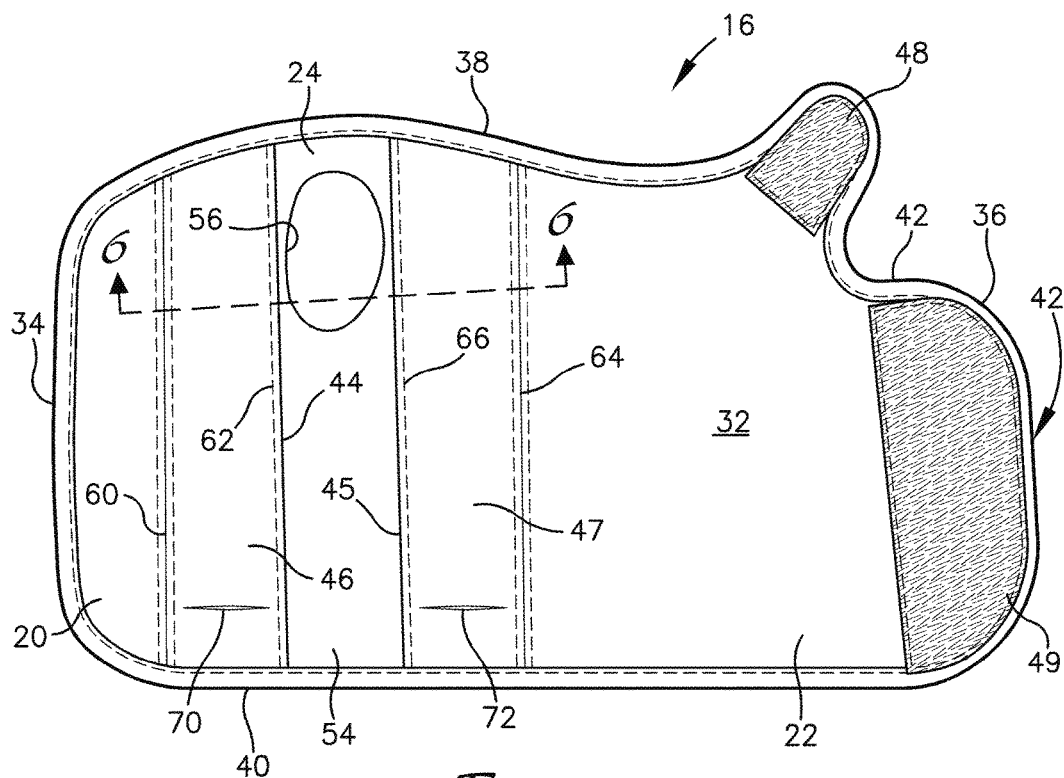
FIG. 5 is an elevation view of the inner surface of the brace, with the webbing removed.
Figure 6:
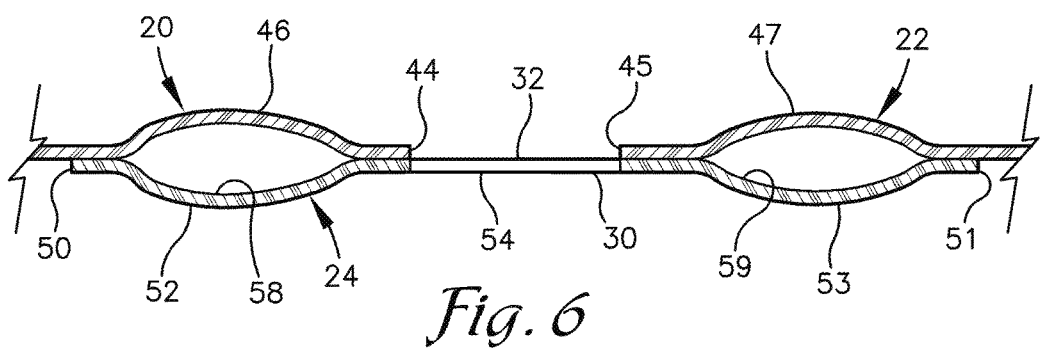
FIG. 6 is a partial cross-section taken along line 6-6 of FIG. 5, showing how the stay pockets of the brace are formed.
Figure 7:
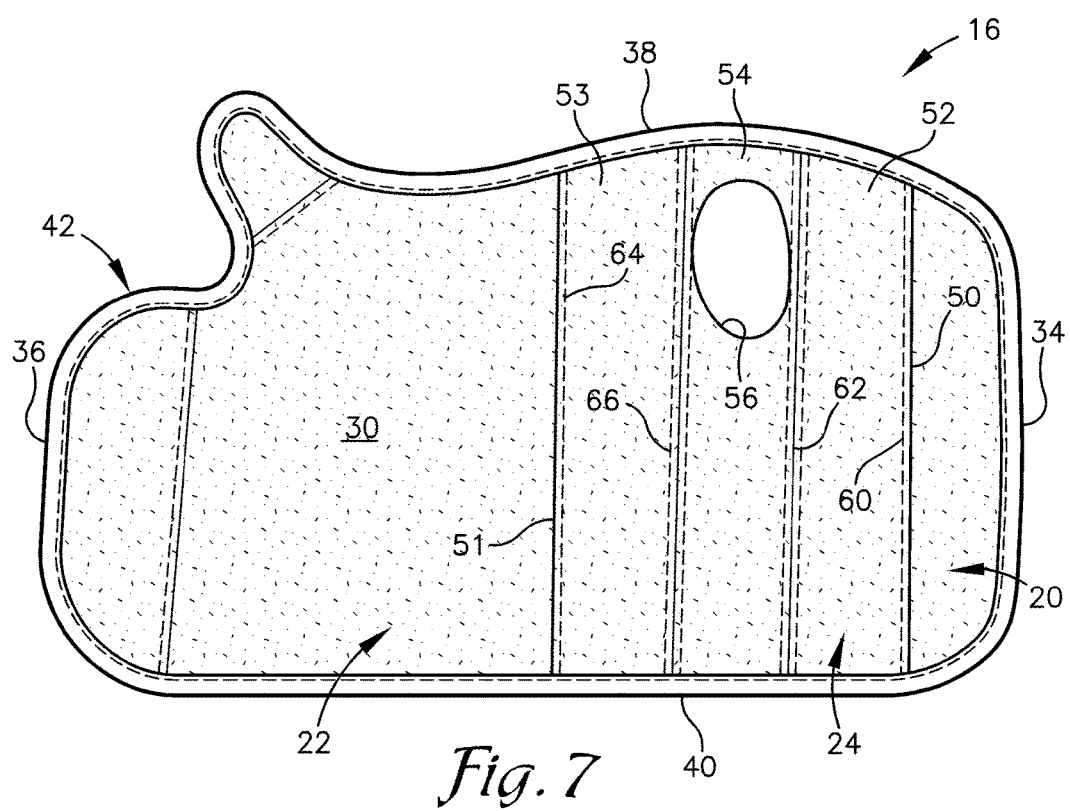
FIG. 7 is an elevation view of the outer surface of the brace, with the stockinet removed.

The wrap 16 is an elongated, flexible pad that may be formed from foamed rubber or any other suitable padding material. It is preferably somewhat elastic but does not have to be. As shown in FIGS. 5-7, the wrap 16 is formed from three sheets of padding 20, 22 and 24 and when assembled, they form outer and inner surfaces 30 and 32, left and right edges 34 and 36, and top and bottom edges 38 and 40. In the preferred embodiment, these padding sheets 20, 22 and 24 are formed from laminated Neoprene, with short loop plush on the outer surface 30 and nylon on the inner surface 32. Finishing tape 42 extends around the periphery of the wrap 16.

The first and second sheets 20 and 22 are best seen in FIGS. 5 and 6. Sheets 20 and 22 are positioned in a laterally spaced apart relationship. Each of these sheets 20 and 22 have an inner side edge 44 and 45 and an inner panel portion 46 and 47, respectively. The panel portions 46 and 47 extend longitudinally along the length of the corresponding sheet 20 or 22 from the top edge 38 to the bottom edge 40 of the wrap 16, substantially adjacent the sheet's corresponding inner side edge 44 or 45. The panels 46 and 47 preferably have a width of about 1½" to accommodate the stay 19 but can be any width, as desired. The outer side edges of the sheets 20 and 22 form the left and right sides edges 34 and 36 of the wrap 16. The sheet 22 is preferably uniquely contoured at the right edge 36 to include attachment flaps 48 and 49 which have hook fastening material on the inner surface 32.

The third or center sheet 24 bridges the first and second sheets 20 and 22. More specifically, this sheet 24 includes opposite side edges 50 and 51 and corresponding overlay portions 52 and 53. A central portion 54 of sheet 24 extends between the overlay portions 52 and 53 of sheet 24 and between sheets 20 and 22. A thumb hole 56 is formed in this central portion of sheet 24. Preferably, the thumb hole 56 is positioned near the wrap's top edge 38. The finishing tape 42 secures the sheets 20, 22 and 24 together at the top and bottom edges 38 and 40.

The overlays 52 and 53 each extend longitudinally along the length of the sheet 24 adjacent the corresponding side edge 50 or 51. The overlays 52 and 53 have a width substantially equal to the width of the panels 46 and 47 of sheets 20 and 22 and overlap the panels 46 and 47 to form a pair of laterally spaced stay pockets 58, 59.

The two stay pockets 58, 59 are formed by two pair of parallel seams 60, 62 and 64, 66 that extend the length of the wrap 16 to secure the overlays 52 and 53 of the center sheet 24 to the panel portions 46 and 47 of sheets 20 and 22. Seam 60 extends through the side edge 50 of the center sheet 24 and the panel portion 46 of the first sheet 20, and seam 62 extends through the center sheet's overlay portion 52 and the inner side edge 44 of the sheet 20. Seam 64 extends through the side edge 51 of the center sheet 24 and the panel portion 47 of the second sheet 22, and seam 66 extends through the center sheet's overlay portion 53 and the inner side edge 45 of the sheet 22.

As seen in FIG. 5, the panel portions 46 and 47 of sheets 20 and 22 include horizontal slits 70 and 72 therethrough, preferably positioned opposite the thumb hole 56, near the bottom edge 40 of the wrap 16. The stay 19 is selectively positioned within and removable from the stay pockets 58, 59 through the slits 70 and 72.

The wrist webbing 18 is shown in FIG. 3. Preferably, it is formed of a breathable, stretchable fabric, such as NATUR-EXX™. The webbing 18 is secured along one side to the left edge 34 of the wrap 16 and along its opposite side to the second sheet 22 immediately adjacent the seam 64. In combination with a portion of the wrap 16, the wrist webbing 18 forms a sleeve through which the right or left hand 12 or 14 is inserted.

Figure 4:
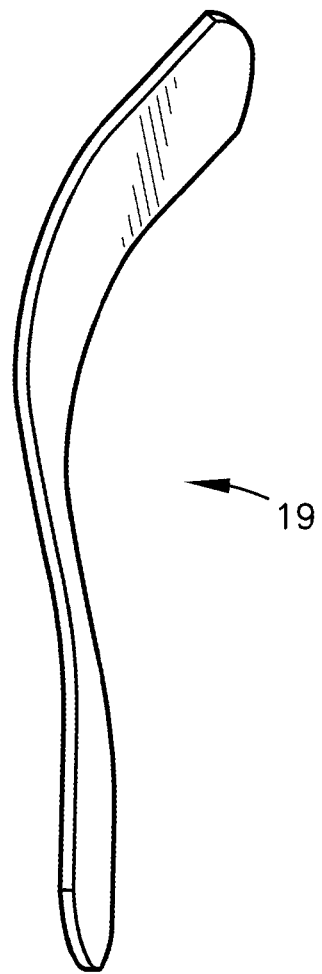
FIG. 4 is a side perspective of a stay support used with the brace.

The stay 19 is shown best in FIG. 4. It is preferably formed of a lightweight metal; however, any rigid material is suitable. The stay 19 is contoured to conform to the shape of the wrist and palm area of the injured hand 12 or 14. The stay 19 is secured within either stay pocket 58, 59 through the slits 70 and 72, depending on which hand 12 or 14 is injured and extends longitudinally along the wrist and palm of the wearer, as seen in FIGS. 1 and 2.

Assembly and Use

The brace 10 is assembled by positioning the first sheet 20 and the second sheet 22 in a laterally spaced apart relationship, with the inner side edges 44 and 45 of each sheet 20 and 22 being substantially parallel. In a preferred embodiment, the inner edges 44 and 45 are approximately 1½" apart. The bridging or central sheet 24 is positioned with its side portions 52 and 53 overlaying the inner portions 46 and 47 of the sheets 20 and 22. The base sheet 20 is secured to the bridging central sheet 24 along seams 60 and 62, and the base sheet 22 is secured to the bridging sheet 24 along seams 64 and 66. It should be understood that while this method of assembly is described herein in connection with a wrist brace, it can be used with any type of brace. Furthermore, this method provides much efficiency, e.g., reduction in sewing time and reduction in the amount of medical grade material required, but creates a clean overall look and provides comfort to the user.

The slits 70 and 72 are cut through the sheets 20 and 22, and the thumbhole 56 is cut through the bridging sheet 24. The fastening hook material is secured to the inner surface 32 of the attachment flaps 48 and 49. The finishing tape 42 is secured around the periphery of the wrap member 16. This effectively closes the top and bottom edges 38 and 40 where the sleeves 20 and 24 and 22 and 24 overlap, to form two pockets 58, 59 into which the stay 19 can be inserted. The wrist webbing 18 is stitched along one side to the left edge 34 of the wrap 16 and is stitched along its other side edge to the sheet 22 adjacent seam 64.

As seen in FIG. 3, a left or right hand 12 or 14 can be inserted through the sleeve formed by the webbing 18 and the wrap 16, with a thumb extending out through the thumbhole 56. The comfort of the brace 10 is enhanced by the use of the wrap's soft padded inner surface 32 and the soft, breathable fabric of the webbing 18.

As seen in FIG. 1, a left hand 12 is shown inserted through the brace 10 and supported therein by the stay 19 which is secured within the pocket 58 formed by seams 60 and 62. The wrap 16 extends over and around the webbing 18 and is secured in place by the hook material on the attachment flaps 48 and 49 engaging the loop material of the outer surface 30 of the wrap 16. Alternatively, if it is the right hand or wrist that is injured, in FIG. 2 the right hand 14 is shown inserted through the brace 10, supported therein by the stay 19 which is secured within the pocket 59 formed by seams 64 and 66. As with the left hand, the wrap 16 extends over and around the webbing 18 and is secured in place by the hook material on the attachment flaps 48 and 49 engaging the loop material of the outer surface 30 of the wrap 16. The stay 19 is selectively removable from and insertable into the pockets 58, 59 through slits 70 and 72. The brace 10 is easily adjusted or removed by pulling on the attachment flaps 48 and 49 to release the hook and loop fastener.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. An orthopedic brace, comprising:
a first layer including a first sheet and a second sheet in a laterally spaced apart relationship,
the first sheet having a first inner side edge, a first inner panel portion, and a first outer side edge that is spaced apart from the first inner panel portion, the first inner panel portion extending a length of the first sheet adjacent the first inner side edge, the first sheet having a first width between the first inner panel portion and the first outer side edge, the first outer side edge forming a first end of the first layer,
the second sheet having a second inner side edge directed toward and oriented parallel to the first inner side edge, a second inner panel portion, and a second outer side edge spaced apart from the second inner panel portion and directed in a direction opposite that of the first outer side edge and forming a second end of the first layer, the second sheet having a second width between the second inner panel portion and the second outer side edge that is greater than the first width, the second sheet forming an attachment flap adjacent the second outer side edge that includes a hook-and-loop fastening material thereon, the second inner panel portion extending a length of the second sheet adjacent the second inner side edge;
a second layer having first and second side edges, a first overlay portion extending a length of the second layer adjacent the first side edge and overlapping the first inner panel portion of the first sheet with the first side edge spaced inwardly apart from the first outer side edge of the first sheet, a second overlay portion extending the length of the second layer adjacent the second side edge and overlapping the second inner panel portion of the second sheet with the second side edge spaced inwardly apart from the second outer side edge of the second sheet, and a center portion extending between the overlay portions and between the first inner side edge of the first sheet and the second inner side edge of the second sheet of the first layer; and
means for securing the first layer to the second layer.

2. The brace of claim 1, wherein the means for securing includes a pair of seams comprising a first seam extending through the second layer's first side edge and the first sheet's first inner panel portion and a second seam extending through the second layer's first overlay portion and the first sheet's first inner side edge, to form a first stay pocket therebetween.

3. The brace of claim 2, wherein the means for securing includes a second pair of seams comprising a third seam extending through the second layer's second side edge and said second sheet's second inner panel portion and a fourth seam extending through the second layer's second overlay portion and the second sheet's second inner side edge, to form a second stay pocket therebetween.

4. The brace of claim 3, further comprising:
a sleeve member secured at a first side along the first outer side edge of the first sheet and at a second side to an inner surface of the second sheet along and adjacent the fourth seam.

5. The brace of claim 3 wherein said center portion includes a thumb opening formed therein.

6. The brace of claim 5 wherein said first stay pocket is adapted to extend longitudinally along a wearer's left wrist.

7. The brace of claim 5 wherein said second stay pocket is adapted to extend longitudinally along a wearer's right wrist.

8. The method of making an orthopedic brace, comprising the steps of:
positioning a first sheet and a second sheet in a laterally spaced apart relationship, with inner side edges of each sheet being parallel, the first sheet having a first width and including one of a hook or a loop material on an outer surface, the second sheet having a second width that is greater than the first width and forming an attachment flap adjacent an outer edge thereof, the attachment flap including the other of the hook or the loop material on an inner surface;
positioning a first side portion of a center sheet over a first inner panel portion of the first sheet and an opposite second side portion of the center sheet over a second inner panel portion of the second sheet;
securing the first sheet and the center sheet together along first and second parallel seams, the first seam extending along a first side edge of the center sheet and bisecting the first sheet, and the second seam extending along the inner side edge of the first sheet and bisecting the center sheet, to form a first stay pocket; and
securing the second sheet and the center sheet together along third and fourth parallel seams, the third seam extending along a second side edge of the center sheet and bisecting the second sheet, and the fourth seam extending along the inner side edge of the second sheet and bisecting the center sheet to form a second stay pocket, the first sheet extending laterally beyond the first seam and the first side edge of the center sheet in a first direction and the second sheet extending laterally beyond the fourth seam and the second side edge of the center sheet in a second direction opposite the first direction.

9. The method of claim 8, further comprising the step of:
forming a thumb hole through a center portion of the center sheet between the first and second sheets.

10. The method of claim 8, further comprising:
securing a sleeve member along an outer edge of the first sheet and to the second sheet along and adjacent the fourth seam and spaced apart from the outer edge of the second sheet.

11. An orthopedic brace, comprising:
a first panel having a first width extending between a first outer edge and a first inner edge, the first panel including one of a hook or a loop material on at least a portion of an outer surface thereof;
a second panel having a second width that is greater than the first width and that extends between a second outer edge and a second inner edge, the second inner edge opposing the first inner edge in a parallel, laterally spaced-apart arrangement, the second outer edge being contoured to form an attachment flap that includes the other of the hook and the loop material on an inner surface thereof;
a bridging center panel extending between the first inner edge of the first panel and the second inner edge of the second panel and partially overlapping the first and second panels, the center panel forming a thumbhole that is positioned between the first inner edge and the second inner edge, the center panel being coupled to the first panel along the first inner edge and including a first terminal edge that is spaced a distance along the first width of the first panel and coupled to the first panel to form a first stay pocket between the first terminal edge and the first inner edge, the center panel being coupled to the second panel along the second inner edge and including a second terminal edge spaced the distance along the second width of the second panel and coupled to the second panel to form a second stay pocket between the second terminal edge and the second inner edge, the first terminal edge being spaced laterally inward from the first outer edge of the first panel and the second terminal edge being spaced laterally inward from the second outer edge of the second panel; and a webbing member coupled to the first panel along the first outer edge and to the inner surface of the second panel at a location adjacent to the second terminal edge of the center panel, the webbing member forming at least a portion of a sleeve into which a wrist of a user is disposable.

\* \* \* \* \*